United States Patent
Potter et al.

(10) Patent No.: US 6,475,181 B1
(45) Date of Patent: Nov. 5, 2002

(54) DRUG PARTICLE DELIVERY

(75) Inventors: Charles David Potter, Standlake (GB); David Stuart Potter, Cowes (GB)

(73) Assignee: PowderJect Research Limited (GB)

( * ) Notice: Subject to any disclaimer, the term of this patent is extended or adjusted under 35 U.S.C. 154(b) by 0 days.

(21) Appl. No.: 09/462,217

(22) PCT Filed: Jul. 3, 1998

(86) PCT No.: PCT/GB98/01963
§ 371 (c)(1),
(2), (4) Date: May 22, 2000

(87) PCT Pub. No.: WO99/01168
PCT Pub. Date: Jan. 14, 1999

(30) Foreign Application Priority Data

Jul. 4, 1997 (EP) .................................. 97304908

(51) Int. Cl.[7] .................................... A61M 5/30
(52) U.S. Cl. ........................ 604/68; 604/70; 604/72
(58) Field of Search ................ 604/68–72, 58, 604/59, 122, 131, 140, 141

(56) References Cited

U.S. PATENT DOCUMENTS

| | | | | |
|---|---|---|---|---|
| 3,788,315 A | * | 1/1974 | Laurens | 128/173 |
| 3,955,571 A | * | 5/1976 | Sunnen et al. | 128/235 |
| 4,790,824 A | * | 12/1988 | Morrow et al. | 604/143 |
| 5,503,627 A | * | 4/1996 | McKinnon et al. | 604/72 |
| 5,520,639 A | * | 5/1996 | Peterson et al. | 604/68 |
| 6,004,286 A | * | 12/1999 | Bellhouse et al. | 604/68 |

FOREIGN PATENT DOCUMENTS

| | | | | |
|---|---|---|---|---|
| WO | WO 94/24263 | * | 10/1994 | C12M/3/00 |
| WO | WO 96/04947 | * | 2/1996 | A61M/5/307 |
| WO | WO 96/12513 | * | 5/1996 | A61M/5/30 |
| WO | WO 96/20022 | * | 7/1996 | A61M/5/30 |
| WO | WO 96/25190 | * | 8/1996 | A61M/5/307 |

* cited by examiner

Primary Examiner—Glenn K. Dawson
Assistant Examiner—Jennifer Maynard
(74) Attorney, Agent, or Firm—Thomas P. McCracken

(57) ABSTRACT

A needleless drug particle delivery device, of the kind in which firing of the drug particles is caused by a sudden gas flow, characterised in that the device comprises a container (14) of compressed gas and a mechanism for releasing the gas from the container to create the gas flow, the mechanism comprising a rupture (20) element for breaching the container and a manually manipulable actuator (27) for moving the element and the container relatively to one another to provide an initial breach whereby gas is released to act on a piston portion (21) to provide a servo action which causes the rupture element and container to move further suddenly relatively to one another to complete the breaching of the container and establish a maximum gas flow from the container.

14 Claims, 5 Drawing Sheets

DRUG PARTICLE DELIVERY

Figure 1:
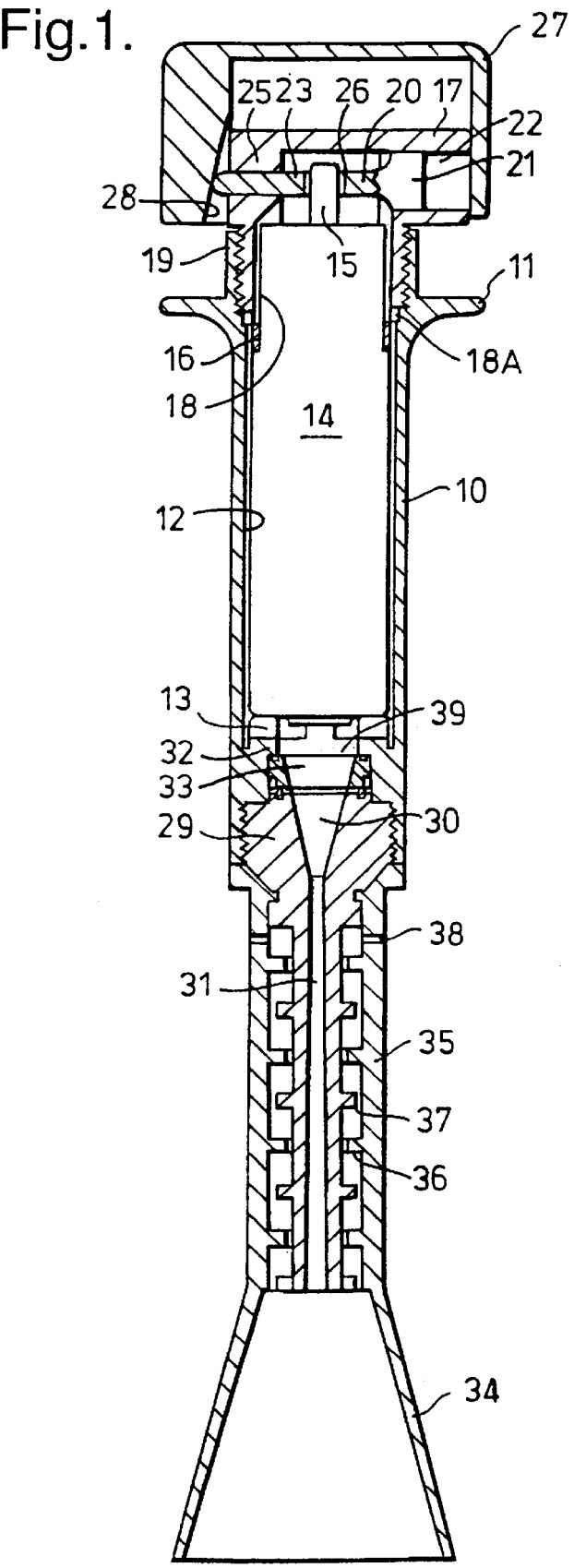

This application is a Section 371 National Stage of International Application No. PCT/GB98/01963, filed Jul. 3, 1998, and enjoys the priority benefit of European Patent Application No. 97304908.3, filed Jul. 4, 1997.

In our earlier international patent applications Nos. WO 94/24263, WO 96/04947, WO 96/12513, WO 96/20022 and WO 96/25190, we disclosed various non-invasive drug delivery systems involving the use of a delivery device such as a needleless syringe or catheter which fires particles consisting of or containing a drug (which term includes genetic material) in controlled doses into body tissue, e.g. through the intact skin, for curative, prophylactic, diagnostic or other medical treatment.

The devices described in the earlier applications are constructed as a tubular nozzle or other lumen, a rupturable element initially closing the passage through the lumen adjacent to the upstream end of the lumen, drug particles located adjacent to the lumen, and energising means for applying to the upstream side of the element a gaseous pressure sufficient to burst the element and to produce within the lumen a supersonic condition and hence cause the particles to be fired from the downstream end of the lumen. In a first type of syringe, the supersonic condition is a supersonic flow of the gas through a nozzle, in which the drug particles are entrained. In that case the particles may be initially located within a rupturable capsule which provides the rupturable element. In the second type of syringe or catheter, the downstream end of the lumen is provided with a bistable diaphragm, which is movable between an inverted position in which it presents outwardly of the lumen a concavity containing the particles, and an everted, outwardly convex, position. The supersonic condition is then a supersonic shockwave which is arranged to snap the diaphragm over from its inverted to its everted position, and to catapult the particles outwardly.

The energising means: disclosed in the earlier applications has, in general, involved the use of a container for compressed gas, the container having an outlet provided with a valve which is opened manually by the operator. Various kinds of valves have been proposed, including a ball valve, in which the ball is pushed off its seat, a piston which is pushed out of sealing engagement with a cylindrical passageway, and a hollow needle which is advanced to pierce a foil closing the container outlet. However, all these solutions suffer from the possible disadvantage that upon manual operation to open the valve, the immediate and subsequent gas flow will depend upon the manipulation of the valve by the operator. In particular, if the valve is not fully opened quickly, the gas may not escape at the desirable maximum flow rate. In contrast, it is desirable that the escape of gas from the container should be substantially immediate, unimpeded, and reliably reproducible on every occasion, so that the characteristics of delivery of the dose of particles, and hence the depth of penetration into the patient., are accurately predetermined.

In accordance with the present invention, a needleless drug particle delivery device, of the kind in which firing of the drug particles is caused by a sudden gas flow, is characterised in that the device comprises a container of compressed gas and a mechanism for releasing the gas from the container to create the gas flow, the mechanism comprising a rupture element for breaching the container and a manually manipulable actuator for moving the element and the container relatively to one another to provide an initial breach whereby gas is released to act on a piston portion to provide a servo action which causes the rupture element and container to move further suddenly relatively to one another to complete the breaching of the container and establish a maximum gas flow from the container.

With this construction,. after the container has been breached manually, and the gas has been released into a volume, which will normally remain fixed while the gas pressure builds up to a value at which resistance to movement of the piston portion is overcome, the servo action will take over and cause full release of the gas in a predetermined manner, irrespective of any uncertain manipulation of the actuator.

The gas flow may be arranged to burst and then flow through a rupturable membrane to cause a shockwave to be transmitted along a lumen to an evertible diaphragm. Alternatively the gas flow may open a drug particle-containing capsule, by bursting a rupturable wall of the capsule or otherwise, to enable the gas flow to entrain particles contained in the capsule.

The rupture element may be a pusher for initially cracking, and subsequently substantially snapping off, a tip of the compressed gas container. Alternatively, the rupture element may be a piercing device, such as a hollow needle, for piercing a foil closing an outlet of the container, or a cutter or blade to cut or slice the outlet of the container.

The actuator may be a slidable or rotary finger or thumb piece provided with a ramp or other cam for providing the initial displacement of the rupture element upon movement of the actuator relatively to a body of the device. When the actuator moves linearly relatively to the rupture element, it may be moved by shortening the device telescopically, eg by pushing a part at the upstream end of the device with a part at the downstream end of the device in contact with the target until the container is breached. In either case the outlet of the container may point towards the upstream end of the device to minimise the possibility of any fragments, which are produced upon rupture of the container, being entrained by the gas and adulterating the particles. Equally, the container outlet may point downstream.

Although the piston portion could be formed on the gas container or by part of a cradle for the gas container, it is most simply provided for movement with, and normally integrated with, the rupture element. In one compact arrangement, the drug particles are arranged to be contained within a capsule, particularly a capsule with rupturable walls, which is mounted within a hollow piston, itself integrated with the rupture element. With this arrangement the rupture element and piston are moved a small distance by manual manipulation of the actuator to breach the container whereafter the gas pressure advances the piston and completes the breaching of the container, until the piston bottoms out. The full gas pressure is then applied to the capsule which is thus opened by rupture of its wall or otherwise, to release the full gas flow through the piston and capsule with the particles entrained in the flow.

In one arrangement of this invention the gas container is a cartridge fitted with a protruding nib-end that can be broken off to reveal an aperture through which the gas can escape. A primary manual leverage action has only to bend over the nib-end a short distance out-of-line in order to initiate a fracture crack and release gas at its junction with the cartridge. The consequent intensification of gas pressure behind the servo-piston propels the nib-end a farther distance out-of-line, progressively enlarging the aperture and, with an increased flowrate of gas, accelerating the movement until the nib-end shears off nearly or completely. This secondary servo action takes place automatically without any additional manual effort or travel, and the nib-end is held captive by the servo-piston element to prevent its interfering with or becoming entrained in the gas stream from the cartridge. This two-stage system of breaching the gas cartridge benefits from the rapidly increasing pressure force applied to the servo-piston, whereas other possible breaching mechanisms may have a constant level or suffer from a diminution of energy after making their initial impact movement.

The depth of dermal penetration of the drug particles is dependent upon the velocity at which the particles are delivered, and this in turn depends upon the velocity of the gas flow in which the particles are entrained, or the velocity of the shockwave when the particles are ejected from an evertible diaphragm. Different drugs need to be delivered to different depths in the tissue at which their activity is maximised. Skin of persons of different age has different penetrability. It is therefore desirable to be able to control accurately, and with reliable reproducibility, the velocity at which the drug particles are delivered, and for the velocity to be adjustable so that a single syringe can be used with different drugs and with persons of different age. We have appreciated that a simple way of being able to adjust the particle velocity is to set the maximum flow of gas from the container. This in turn can be achieved by adjusting the extent to which the container is breached, when the breaching has been completed, thereby utilising an adjustable restriction to the outflow of gas from the container. A simple way of providing such adjustment in the maximum gas flow is to provide an adjustable stop which limits the stroke of the piston portion at a set position. For example, when the container is a cartridge fitted with a protruding nib-end, progressive bending of the nib-end out-of-line, will progressively open the cartridge outlet and hence progressively increase the gas flow. Limiting the stroke of the piston portion, by appropriate setting of the stop, will then provide a predetermined gas flow from the cartridge.

Some examples of needleless syringes constructed in accordance with the present invention are illustrated diagrammatically in the accompanying drawings, in which:

FIGS. 1 to 4 and 6 are central sections through five different syringes;

FIG. 5 is a section taken on the line V—V in FIG. 4; and,

FIG. 7 is a section, corresponding to FIG. 1 but showing a modification.

The syringe of FIG. 1 has a barrel 10, having, near its upper end, an annular wing 11. The barrel is provided on its inner wall with a plurality of circumferentially spaced axial ribs 12 defining between adjacent ones of the ribs a plurality of channels. Near its lower end the barrel is provided with a number of radially extending castellations 13. The barrel thus provides a housing for a sealed cartridge 14 of compressed helium at a pressure of, typically, between 40 and 80 bar. The cartridge has a frangible tip 15. When preparing the syringe for use the cartridge is inserted into the barrel 10 until it comes to rest on castellations 13, and is then secured in place by the bottom of a downwardly extending skirt 16 on an upper housing part 17 which is screwed into an upper end portion 19 of the barrel 10. The inner wall of the skirt 16 is also provided with a plurality of circumferentially spaced axial ribs 18 defining between adjacent ones of the ribs a plurality of channels which communicate at their lower ends via an annular groove 18A with the upper ends of the channels between the ribs 12.

The housing 17 contains a rupture element 20 having an annular piston portion 21, which slides within a cylindrical portion 22 of the housing, and a leg 23 which is slidable within a through hole in an end wall 25 of the housing. The leg 23 has a gate 26 through which the tip 15 of the cartridge projects. Slidable over and around the housing 17 is an actuator cap 27 having a chamfered cam surface 28 initially in light engagement with the tip of the leg 23.

The lower part of the syringe is very similar to that illustrated in FIG. 1 of WO 94/24263. Thus the internally screw threaded lower end of the barrel 10 is screwed over the outside of a nozzle 29 containing a passageway with a short upstream convergent section 30 and a downstream longer divergent section 31. Sandwiched between a shoulder 32 on the barrel 10 and the upper end of the nozzle 29 is a drug capsule 33. This is constructed like the capsule illustrated in FIG. 8 of WO 94/24263 and comprises an annular ring, having a frusto conical internal periphery surrounding a compartment containing the drug particles to be injected. The top and bottom of the compartment are closed by rupturable Mylar diaphragms which are bonded and sealed to the upper and lower walls of the ring so that the capsule forms a self contained sealed unit. The capsule is sealed to the shoulder 32 and nozzle 29 by interposed 0 rings recessed into the capsule ring and nozzle respectively. The frusto conical internal periphery of the capsule ring forms a continuation of the frusto conical upstream section of the passage through the nozzle 29.

The nozzle 29 is surrounded, downstream of its screw threaded connection to the barrel 10, by a tubular portion providing a divergent spacer shroud 34 and a cylindrical silencer part 35, made and assembled as described in WO 94/24263. The inner surface of the cylindrical part 35 is integrally formed with a number of axially spaced, radially inwardly projecting baffles 36. The outer surface of the nozzle is complementarily provided with a series of radially outwardly extending baffles 37, each axially spaced equidistant between a respective adjacent pair of the baffles 35. A ring of exhaust vents 38 is formed in the cylindrical part 35, adjacent to its upper end.

In use the syringe is prepared, if not supplied ready prepared, by unscrewing the barrel 10 from the nozzle 29, inserting a capsule 33 and screwing the barrel and nozzle together again. The housing 17 is unscrewed from the barrel 10 and a helium cartridge 14 inserted, prior to screwing the housing and barrel together again.

To operate the syringe, the downstream wider end of the spacer shroud 34 is pressed against the patient's skin and, for example, with the cap in the palm of the operator's hand, and his first and second fingers engaging beneath the wing 11, the cap is pressed down over the housing 17 so that the chamfered cam surface 28 forces the rupture element 20 to move slightly to the right as seen in FIG. 1. This begins to bend and break off the tip 15 of the cartridge 14, as a result, perhaps, of a preformed nick or other point of weakness in the tip, which may be made of an aluminium alloy, and hence breaches the integrity of the cartridge. This releases some gas from the cartridge and the gas builds up pressure behind the annular surface of the piston head 21 around the leg 23. The gas pressure then provides a servo action which suddenly forces the rupture element 20 to the right as seen in FIG. 1, thereby snapping fully open the frangible end of the cartridge tip 15. The compressed helium in the cartridge is then free to flow quickly through the channels in the wall of the skirt 16 and in the wall of the barrel 10 around the cartridge 14, into a rupture chamber 39 formed within the barrel upstream of the capsule 33. When the pressure has built up sufficiently in this rupture chamber, the diaphragms of the capsule 33 are ruptured and a supersonic flow of gas through the nozzle 29, in which the drug particles from within the capsule 33 are entrained, is released. These particles impinge upon, and penetrate, the patient's skin, to the required depth. The shockwave reflected from the patient's skin is transmitted back through the tortuous passage in the silencer between the interdigitating baffles 36 and 37, and is eventually vented to atmosphere through the vents 38. Depending upon the circumstances, the syringe, is then disposed of or recharged with a new drug capsule and gas cartridge.

Figure 2:
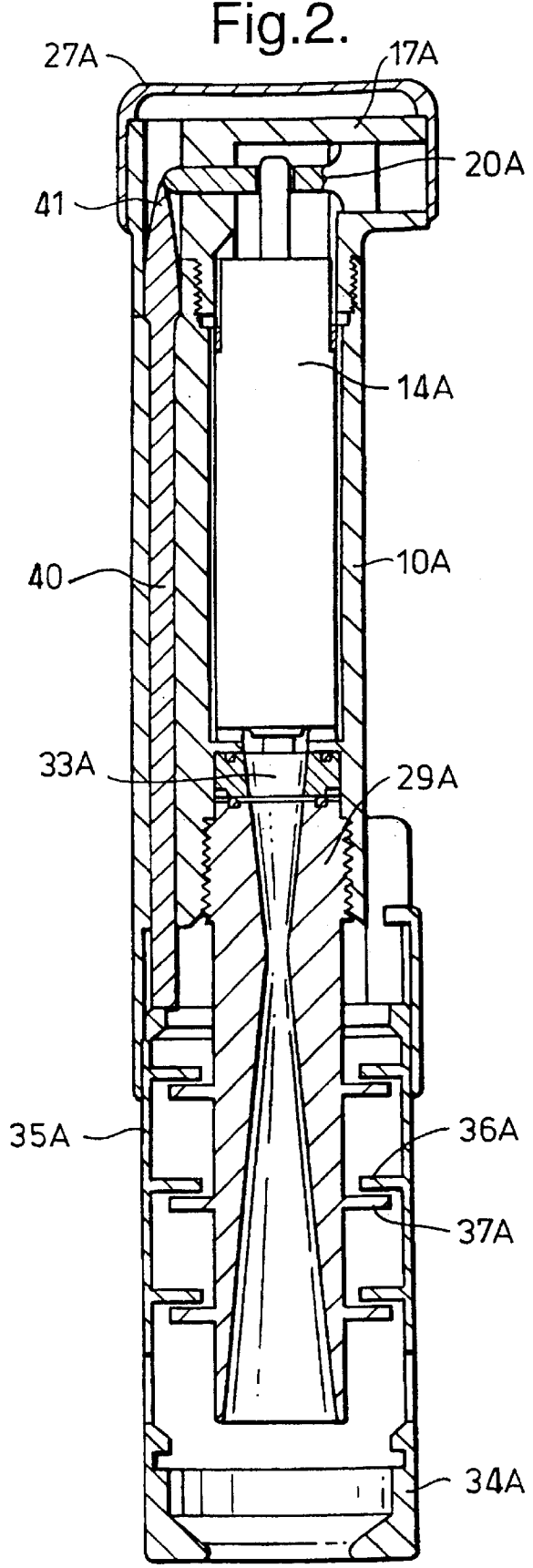

The syringe shown in FIG. 2 is similar in construction and function to that of FIG. 1 and corresponding parts are given the same reference numerals with the suffix A. The essential differences are as follows. The housing 17A, containing the rupture element 20A is screwed to the barrel 10A and is fixed relatively to the actuator cap 27A. The left hand side of the barrel 10A as seen in FIG. 2, has an enlarged thickness containing a longitudinal bore in which there slides an actuator spear 40 having a chamfered tip 41 which initially loosely engages the leg of the rupture element 20A. The lower end of the spear 40 abuts against the upper end of a cylindrical shroud 35A which is slidably mounted in the bottom of the barrel 10A. The downstream end of the shroud 35 provides a spacer 34A extending beyond the downstream end of the nozzle 29A but is not flared as, in this case, this is unnecessary owing to the larger divergence of the downstream section of the passage through the nozzle 29A, which allows sufficient spread of the drug particles. However, the cylindrical portion 35A is provided with baffles 36A, interdigitating with baffles 37A to provide a silencer.

In operation the downstream end of the spacer portion 34A is pressed against the patient's skin and axial pressure is applied to the cap 27A. This causes the parts other than the shroud and spear element 40 to move towards the target, hence causing the chamfered tip 41 of the spear 40 to force the rupture element 20A to the right as seen in FIG. 2 and crack open the tip of the cartridge 14A. Thereafter the operation is as described with reference to FIG. 1. It will be appreciated that as the nozzle 29A moves downwards relatively to the shroud 35A, the baffles 36A and 37A move to positions in which each is substantially equidistant between a pair of the others to maximise the silencing effect.

Figure 3:
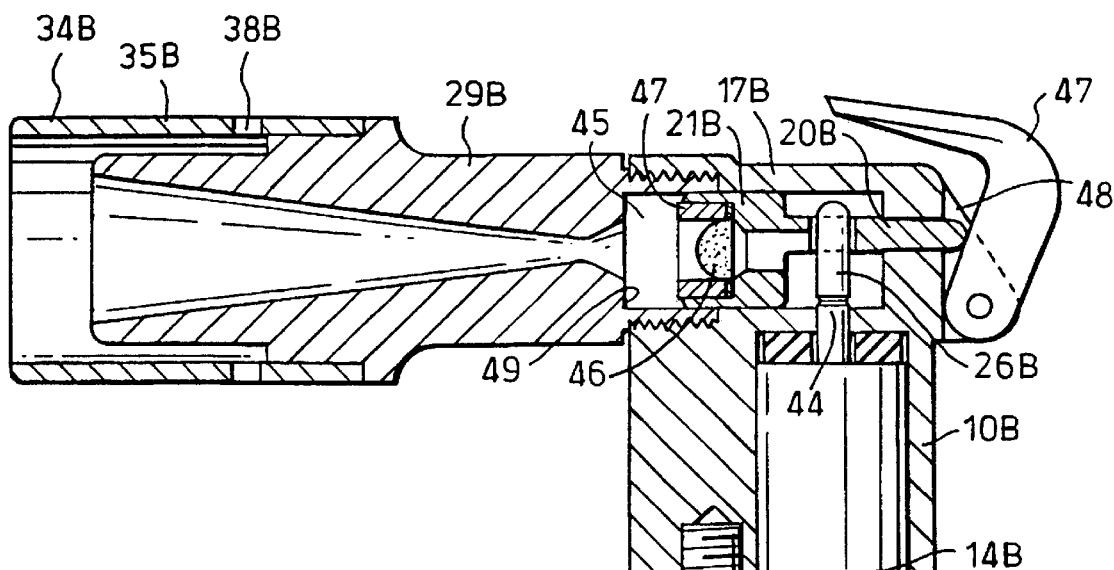

In the example shown in FIG. 3, parts analogous in function to those in FIG. 1 are given the same reference numeral with the suffix B.

In this example the barrel is in two parts 10B which are held together by a screw 43, with the helium cartridge 14B sandwiched between them. A line of weakness 44 in the tip 26B can be seen. The upper part 10B of the barrel, as seen in FIG. 3, is formed integrally with a housing 17B containing a slidable rupture element 20B. The nozzle 29B is connected by a screw thread to the upper barrel portion 10B and provides, in. conjunction with the housing 17B, a cylinder 45 in which the piston end 21B of the element 20B slides. The end of the rupture element beyond the piston 21B carries a drug particle capsule in the form of a blister pack 46 having a peripheral flange which is secured in a countersunk recess in the element 20B by a cylindrical retaining element 47 which is a force fit into the recess.

The nozzle 29B has a cylindrical shroud which provides both a spacer portion 34B, and a silencer portion 35B surrounding the downstream end of the nozzle 29B with a clearance, which may provide a tortuous path through which a shockwave may be vented to atmosphere through vents 38B. In this case an actuator is formed by a thumb piece of angular shape which is pivoted at one end between clevis flanges 48 projecting integrally from the upper barrel portion 10B.

The syringe is operated by grasping the barrel and applying anti-clockwise pressure, as seen in FIG. 3, to the actuator 47. This displaces the rupture element 20B slightly to the left, cracking the tip 26B of the cartridge 14B and releasing a precursor gas flow into the space behind the piston 21B. The piston is thus forced sharply to the left, as seen in FIG. 3, fully opening the cartridge under the servo action of the gas, until the element bottoms out against the shoulder 49 in the nozzle 29B. Further build up of gas behind the capsule 46 eventually causes the walls of the blister pack to rupture and to release through the nozzle 29B a supersonic gas flow in which the drug particles are entrained, to impinge and penetrate the patient's skin against which the open end of the spacer portion 34B of the shroud is pressed.

Figure 4:
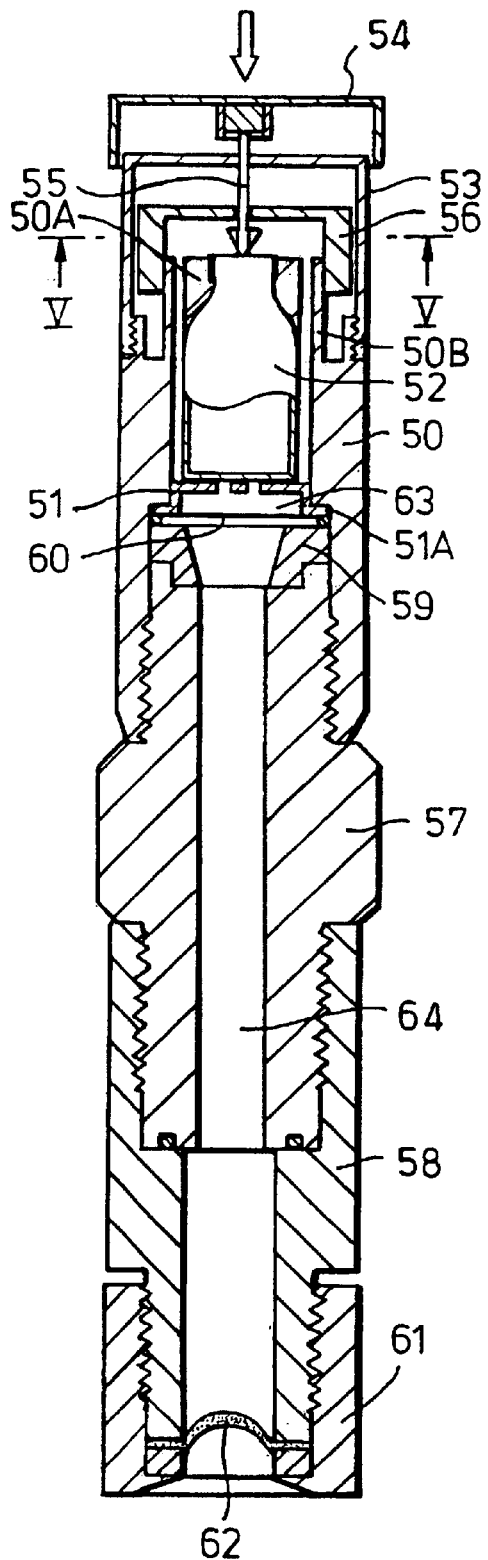
Figure 5:
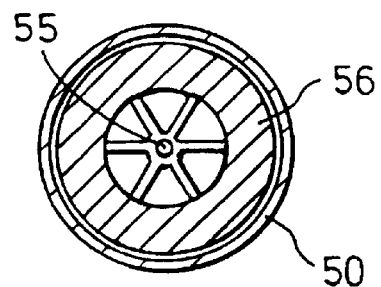

The FIGS. 4 and 5 example shows another gas release mechanism in accordance with the invention but for generating a shock wave to evert a drug particle-containing diaphragm, as described in WO 96/20022, instead of for generating a supersonic gas flow in which drug particles are entrained, as disclosed in WO 94/24263. Indeed, the FIG. 4 example differs only from the FIGS. 1 to 3 example of WO 96/20022 in the gas release mechanism.

Thus the FIG. 4 syringe has an upper tubular portion 50, having a separate perforated internal support 51 on which there rests a cartridge 52 of compressed helium. A housing 53, is screwed to the tubular portion 50. An actuator cap 54, slides over the housing and is provided with a downwardly projecting rupture element 55, having, at its lower end, a sharp pointed head arranged to breach a foil seal on the upper end of the cartridge 52. The rupture element 55 slides through a central hole in a piston element 56, which can slide down around the cylindrical outer surface of an upward extension 50A of the portion 50, the piston having a central aperture smaller than the head of the element 55. The extension 50A is formed with a ring of axial passages 50B and an internal profile which forms a collar around and complements the neck of the cartridge 52 to hold the cartridge down on the support 51.

The tubular portion 50 is screw threaded to a central tubular portion 57 which in turn is screw threaded to a lower tubular portion 58. Sandwiched between a shoulder of the upper tubular portion 50 and an insert 59 in the central tubular portion 57, is a peripheral ring of a rupturable diaphragm 60 and a flange 51A of the support 51. The downstream end of the lower tubular portion 58 has screwed onto it a gland nut 61 and sandwiched between the lower end of the portion 58 and an inwardly projecting shoulder of the nut 61 is a peripheral flange of an evertible diaphragm 62 which initially presents downstream a concave configuration containing drug particles. The construction of this diaphragm and the manner in which the drug particles are retained is more fully described in WO 96/20022.

In operation of the FIG. 4 syringe, the barrel formed by the parts 50, 57, 58 is grasped in the hand and with the downstream end of the device pressed against the patient's skin, the actuator cap 54 is depressed by the operator's thumb. As a result the tip of the rupture element 55 breaches the foil closing the outlet of the cartridge 52, whereupon gas can escape up through the discontinuous central portion of the piston 56 and thereupon act upon the upper surface of the piston. This provides a servo action causing the piston to move sharply downwardly, carrying the enlarged tip of the element 55 further into the cartridge to open the cartridge fully and allow the escape of gas down through the passages 50B around the cartridge 52, and through the support 51 into a rupture chamber 63. Here the gas pressure quickly builds up until the diaphragm 60 ruptures releasing a supersonic gaseous shockwave along the shock tube 64 formed by the passage through the parts 57 and 58, thus causing the diaphragm 62 suddenly to evert to a convex position and catapult the drug particles into the patient's skin.

Figure 7:
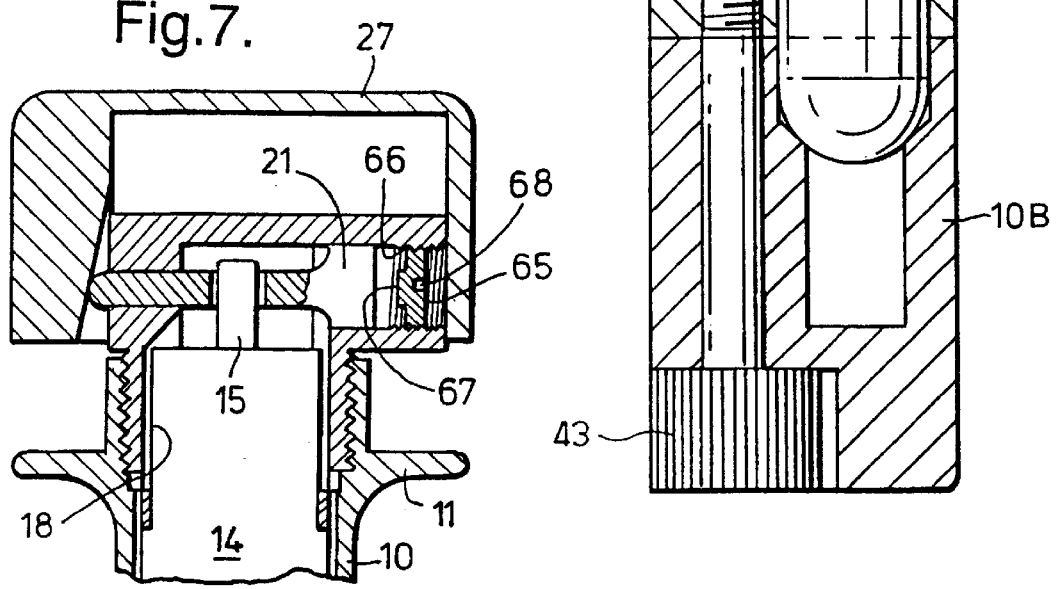

FIG. 7 shows a modification of FIG. 1, in which an adjustable stop 65 is screwed into a threaded portion of the cylinder 22. The stop 65 has a projected abutment 67 against which the end of the piston portion 21 will come to rest when the gas release mechanism is operated, thereby limiting the extent to which the frangible tip 15 is bent sideways. The position of the stop 65 can be adjusted by pulling off the cap 27, which is a push fit, and rotating the stop 65 by applying a screwdriver to a slot 68 in the stop, prior to refitting the cap 27.

Figure 6:
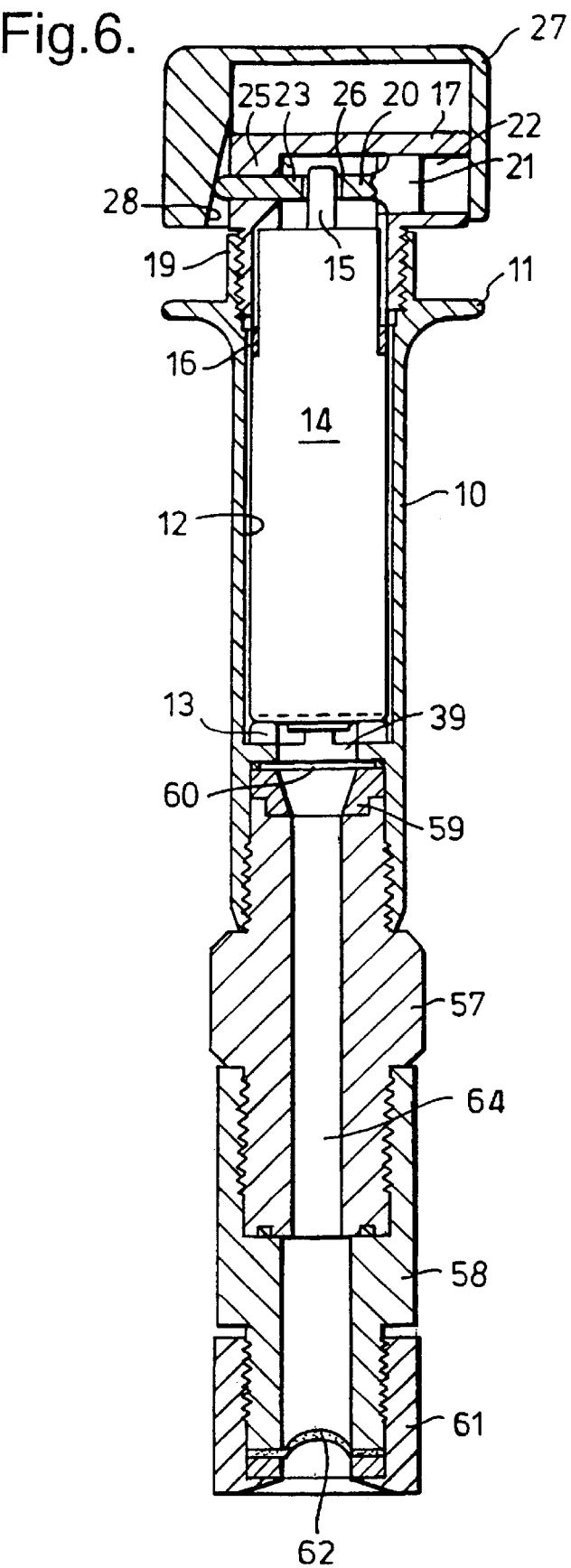

Of course it would be possible to combine the gas release mechanism of any one of FIGS. 1 to 3 or 7 with the rupturable diaphragm, shock tube and evertible diaphragm of FIG. 4, as shown in FIG. 6, which shows a hybrid of FIGS. 1 and 4. Equally a gas release mechanism, similar to that of the FIG. 4 example could be used to promote the particle-entraining gas flow of the FIGS. 1 to 3 or 7 examples.

The new gas release mechanism may be used, not only in a syringe, but also other circumstances in which firing of particles by a sudden gas flow is needed, for example in a catheter as described in WO 96/20022.

What is claimed is:

1. A needleless particle delivery device for firing particles at a target surface using a sudden gas flow, characterised in that said device comprises a container of compressed gas and a mechanism for releasing gas from the container to create a gas flow through the device, the mechanism comprising an element for breaching the container and a manually manipulable actuator for moving the element and the container relative to one another to provide an initial breach whereby gas is released to help provide a servo action sufficient to suddenly move the element and container farther relative to one another, thereby finishing the breach of the container to establish a maximum gas flow therefrom.

2. A device according to claim 1, further comprising a lumen having an upstream end, and a downstream end. wherein the upstream end is adjacent to the container and has a rupturable membrane which is arranged over and closes off the upstream end of the lumen prior to being burst by release of the gas flow into the device.

3. A device according to claim 1, further comprising a particle-containing capsule which is opened by the gas flow when released into the device.

4. A device according to claim 1, wherein the element for breaching the container is use for initially cracking, and subsequently substantially snapping off, a tip of the container.

5. A device according to claim 1, wherein the actuator comprises a finger or thumb piece with a cam attached thereto.

6. A device according to claim 1 further comprising an adjustable stop for limiting travel of the element, whereby the maximum gas flow from the container is adjustable.

7. A device according to claim 1, wherein the servo action is provided by the gas released by the initial breach acting upon a piston portion that is integral with the element.

8. A device according to claim 2 further comprising an evertible diaphragm arranged over the downstream end of the lumen.

9. A device according to claim 2, wherein the rupturable membrane is provided by a particle-containing capsule arranged over and closing off the upstream end of the lumen.

10. A particle delivery device for firing particles at a target surface using a sudden gas flow, characterized in that said device comprises a container of compressed gas, an element for breaching the container to release the compressed gas when the element and container are moved relative to each other, and an adjustable stop for limiting the relative movement of the element and container, whereby said adjustable stop provides an adjustable restriction on the maximum outflow of gas from the container.

11. A method for delivering particles to a target surface, sad method comprising:

(a) providing a particle delivery device that comprises a container of compressed gas, a sealed capsule containing the particles, and a mechanism for releasing gas from the container to create a gas flow through the device, the mechanism comprising an element for breaching the container and a manually manipulable actuator for moving the element and the container relative to one another to provide an initial breach whereby gas is released to help provide a servo action sufficient to suddenly move the element and container further relative to one another, thereby finishing the breach of the container to establish a maximum gas flow therefrom; and (b) actuating the device against the target surface, thereby delivering said particles to said surface.

12. The method of claim 11, wherein said particles are delivered into body tissue to provide for curative, prophylactic, diagnostic or other medical treatment.

13. A method for delivering particles to a target surface, said method comprising:

(a) providing a particle delivery device that comprises a container of compressed gas, an element for breaching the container to release the compressed gas when the element and container are moved relative to each other, a sealed capsule containing the particles, and an adjustable stop for limiting the relative movement of the element and container, whereby said adjustable stop provides all adjustable restriction on the maximum outflow of gas from the container and (b) actuating the device against the target surface, thereby delivering said particles to said surface.

14. The method of claim 13 wherein said particles are delivered into body tissue to provide for curative, prophylactic, diagnostic or other medical treatment.

* * * * *